(12) United States Patent
Zavislan

(10) Patent No.: US 8,606,343 B2
(45) Date of Patent: *Dec. 10, 2013

(54) SYSTEM AND METHOD FOR CONFOCAL IMAGING WITHIN DERMAL TISSUE

(75) Inventor: James M. Zavislan, Pittsford, NY (US)

(73) Assignee: Lucid, Inc., Rochester, NY (US)

( * ) Notice: Subject to any disclaimer, the term of this patent is extended or adjusted under 35 U.S.C. 154(b) by 1220 days.

This patent is subject to a terminal disclaimer.

(21) Appl. No.: 11/784,128

(22) Filed: Apr. 5, 2007

(65) Prior Publication Data

US 2007/0287921 A1 Dec. 13, 2007

Related U.S. Application Data

(62) Division of application No. 09/658,736, filed on Sep. 11, 2000, now Pat. No. 7,225,010, which is a division of application No. 08/942,431, filed on Oct. 1, 1997, now Pat. No. 6,424,852.

(60) Provisional application No. 60/028,847, filed on Oct. 18, 1996.

(51) Int. Cl.
*A61B 5/00* (2006.01)

(52) U.S. Cl.
USPC ........... 600/407; 600/476; 359/368; 359/391; 359/801

(58) Field of Classification Search
USPC .......... 600/407, 425, 476–477; 359/368–385, 359/390–393, 798, 801
See application file for complete search history.

(56) References Cited

U.S. PATENT DOCUMENTS

| 4,385,634 A | 5/1983 | Bowen |
| 4,442,844 A | 4/1984 | Navach |
| 4,515,165 A | 5/1985 | Carroll |
| 4,570,638 A | 2/1986 | Stoddart et al. |
| 4,807,979 A * | 2/1989 | Saccomanno et al. ........ 359/368 |
| 5,120,953 A | 6/1992 | Harris |
| 5,146,923 A | 9/1992 | Dhawan |
| 5,195,522 A | 3/1993 | Pytel et al. |

(Continued)

FOREIGN PATENT DOCUMENTS

| AU | A-11045/88 | 8/1988 |
| CH | 669 325 A5 | 3/1989 |

(Continued)

OTHER PUBLICATIONS

Machine Translation of JP7-333517A Dec. 1995.*

(Continued)

*Primary Examiner* — Ruth S Smith
(74) *Attorney, Agent, or Firm* — Kenneth J. Lukacher Law Group

(57) ABSTRACT

An improved system for confocal imaging within dermal tissue of a patient is provided which minimizes instability in confocal images by reducing the relative motion of the tissue with respect to the confocal imaging optics of the system. The system includes a mechanism for maintaining an area of skin tissue under stress by application of force at the edges of the area, and an imaging head coupled to this mechanism for imaging the stressed skin. The mechanism includes a mechanical structure, such as a platen, brace, or attachment, which both supports the imaging head of the system and applies stress to a limited surface area of the tissue to minimize skin motion during confocal imaging.

32 Claims, 10 Drawing Sheets

(56) References Cited

U.S. PATENT DOCUMENTS

| | | |
|---|---|---|
| 5,349,961 A | 9/1994 | Stoddart et al. |
| 5,371,368 A | 12/1994 | Alfano et al. |
| 5,524,636 A | 6/1996 | Sarvazyan et al. |
| 5,557,452 A | 9/1996 | Harris |
| 5,598,269 A * | 1/1997 | Kitaevich et al. ............ 356/399 |
| 5,606,971 A | 3/1997 | Sarvazyan |
| 5,701,902 A | 12/1997 | Vari et al. |
| 5,719,700 A | 2/1998 | Corcuff et al. |
| 5,722,398 A | 3/1998 | Ishihara et al. |
| 5,730,133 A | 3/1998 | Godik |
| 5,769,076 A | 6/1998 | Maekawa et al. |
| 5,787,887 A | 8/1998 | Klingenbeck-Regn |
| 5,788,634 A | 8/1998 | Suda et al. |
| 5,788,639 A | 8/1998 | Zavislan et al. |
| 5,833,633 A | 11/1998 | Sarvazyan |
| 5,833,634 A | 11/1998 | Laird et al. |
| 5,840,023 A | 11/1998 | Oraevsky et al. |
| 5,842,995 A | 12/1998 | Mahadevan-Jansen et al. |
| 5,848,177 A | 12/1998 | Bauer et al. |
| 5,851,181 A | 12/1998 | Talmor |
| 5,860,967 A | 1/1999 | Zavislan et al. |
| 5,880,880 A | 3/1999 | Anderson et al. |
| 5,995,283 A | 11/1999 | Anderson et al. |
| 5,999,836 A | 12/1999 | Nelson et al. |
| 6,032,071 A | 2/2000 | Binder |
| 6,197,575 B1 | 3/2001 | Griffith et al. |
| 6,263,233 B1 | 7/2001 | Zavislan et al. |
| 6,509,161 B1 | 1/2003 | Barker et al. |
| 6,745,067 B1 | 6/2004 | Zavislan et al. |
| 6,937,886 B2 | 8/2005 | Zavislan |
| 7,225,010 B1 | 5/2007 | Zavislan |
| 7,711,410 B2 | 5/2010 | Zavislan et al. |
| 2010/0137710 A1 | 6/2010 | Zavislan |

FOREIGN PATENT DOCUMENTS

| | | |
|---|---|---|
| DE | 32 31 483 A1 | 3/1984 |
| EP | 0 683 386 A1 | 11/1995 |
| JP | 07333517 A * | 12/1995 |
| WO | WO 88/05284 | 7/1988 |
| WO | WO 96/21938 | 7/1996 |

OTHER PUBLICATIONS

Jester et al., In-Vivo Real-Time Confocal Imaging, Journal of Electron Microscopy Technique, vol. 18, No. 1, pp. 50-60, May 1991.

Brumberg et al., "Hand-held contact microscope for medical applications," Soviet Journal of Optical Technology, Jan. 1974, vol. 41, No. 1.

Corcuff et al., Morphometry of human epidermis in vivo by real-time confocal microscopy, Arch Dermatol Res. 1993, 285, pp. 475-481.

Rajadhyaksha, et al., "In Vivo Confocal Scanning Laser Microscopy of Human Skin: Melanin Provides Strong Contrast" The Journal of Investigative Dermatology, vol. 104, No. 6, Jun. 1995, pp. 1-7.

Corcuff et al., In vivo Vision of the Human Skin with the Tandem Scanning Microscope, Dermatology, vol. 186, pp. 50-54, (1993).

Koester, C., Scanning mirror microscope with optical sectioning characteristics: applications in ophthalmology, Applied Optics, vol. 19, No. 11, pp. 1749-1757, 1980.

Maurice, D., Cellular Membrane Activity in the Corneal Endothelium of the Intact Eye, Experientia, vol. 24, No. 11, pp. 1094-1095, 1968.

Maurice, D., A Scanning Slit Optical Microscope, Investigative Ophthalmology, vol. 13, No. 12, pp. 1033-1037, 1974.

New, K. et al., In Vivo Imaging of Human Teeth and Skin Using Real-Time Confocal Microscopy, Scanning, vol. 13, pp. 369-372, 1991.

Delaney et al., Fibre Optic Confocal Imaging (FOCI) for subsurface microscopy of the colon in vivo, J. Anat. 184, pp. 157-160, (1994).

Delaney et al., Novel Microscopy Using Fibre Optic Confocal Imaging and Its Suitability for Subsurface Blood Vessel Imaging in Vivo, Clinical and Experimental Pharmacology and Physiology, 20, pp. 197-198, (1993).

Office Action dated Aug. 1, 2011 of U.S. Appl. No. 12/658,036.

* cited by examiner

SYSTEM AND METHOD FOR CONFOCAL IMAGING WITHIN DERMAL TISSUE

This application is a divisional of U.S. patent application Ser. No. 09/658,736, filed Sep. 11, 2000, now U.S. Pat. No. 7,225,010, which is a divisional of U.S. patent application Ser. No. 08/942,431, filed Oct. 1, 1997, now U.S. Pat. No. 6,424,852, which claims the benefit of priority from U.S. Provisional Application Ser. No. 60/028,847, filed Oct. 18, 1996.

FIELD OF THE INVENTION

The present invention relates to a confocal imaging system for in vivo clinical examinations of dermal and subdermal tissues, and particularly to a confocal imaging system of a patient's skin tissue which minimizes instability in confocal images by reducing the relative motion of the tissue with respect to the confocal imaging optics of the system. This invention is especially suitable for providing an instrument or attachment for dermal pathological applications.

BACKGROUND OF THE INVENTION

Systems have been proposed for confocal scanning of skin, such as described in Rajadhyaksha et al., "In vivo Confocal Scanning Laser Microscopy of Human Skin: Melanin provides strong contrast," The Journal of Investigative Dermatology, Volume 104, No. 6, June 1995, pages 1-7. These systems have confocal optics which direct light to the patient's skin tissue and image the returned reflected light. Such optics have a limited field of view of the patient's skin tissue, which for example may cover a tissue area less than one millimeter wide. One problem with these systems is that motion of the patient during confocal imaging can cause the tissue area being imaged to move relative to the system's confocal optics, shifting the field of view of the tissue area with respect to the optics. Consequently, confocal images from such systems may appear unstable to the viewing physician, making it difficult for the physician to observe dermal structures of interest. Even slight motion of the patient's skin tissue, such as due to involuntary muscle movement in adjacent tissue or from a circulatory pulse, can cause dermal structures of a confocal image to appear to move in and out of the imaged tissue area.

SUMMARY OF THE INVENTION

Accordingly, it is the principal object of the present invention to provide an improved system for confocal imaging within dermal and subdermal tissue of a patient which minimizes instability in confocal images by reducing the relative motion of the tissue with respect to the confocal imaging optics of the system.

It is another object of the present invention to provide an improved system for confocal imaging of tissue having a mechanical structure, such as a platen, brace, or attachment which both supports the confocal imaging optics of the system and applies stress to a limited surface area of the tissue to minimize skin motion during confocal imaging.

Briefly described, the system embodying the present invention includes a mechanism for maintaining an area of skin tissue under stress by application of force at the edges of the area, and an imaging head coupled to this mechanism for imaging the stressed skin. The mechanism and imaging head provide an integrated assembly. In one embodiment, the mechanism of the system for maintaining an area of skin tissue under stress is provided by a platen, which is positionable with respect to the patient having the skin tissue to be examined. The imaging head is coupled to the platen and is positioned for imaging through an orifice in the platen. To position the platen with respect to the patient, the patient is supported by a table and the platen rides in a carriage upon rails over the patient. The carriage and platen assembly may be temporarily locked in position upon the rails. Another mechanism is provided in the system for moving the platen from an up position in the carriage, where the platen is spaced from the patient, to a down position onto the surface of the skin tissue of the patient, such that in the down position the force of the platen stresses the skin-tissue within the orifice of the platen.

In a second embodiment, the mechanism of the system for maintaining an area of skin tissue under stress is provided by a brace supporting the imaging head. The brace has an opening through which the imaging head images the skin tissue. The brace is restrained by straps to the body part of the patient having the skin tissue in order to force the brace against the skin tissue, thereby stressing the skin tissue within the opening of the brace. The brace may further include an upper lamination, coupled to the imaging head, and a lower lamination, coupled to the restraining straps, which provides the opening of the brace. The lower lamination has slots for receiving the upper lamination in which the upper lamination is movable within the slots over the lower lamination and temporarily fixable within respect to the lower lamination. The upper lamination has an aperture (or window) substantially smaller than the opening in the lower lamination. Through the aperture of the upper lamination, the imaging head images the stressed skin tissue within the opening of the lower lamination.

In a third embodiment, the mechanism of the system for maintaining an area of skin tissue under stress is provided by an attachment having an inner window member and a flexible diaphragm member extending radially from the inner member. A suction mechanism is provided for creating a vacuum between the attachment and the surface of the skin tissue to force the skin tissue against the inner member, thereby stressing the skin tissue adjacent to the inner member. The imaging head images the stressed skin tissue through the window member. The diaphragm member may further include a semi-rigid ring along its outer periphery and an annular protruding section which defines inner and outer cavities when the attachment is adjacent to the skin tissue. The suction mechanism may then selectively create suction in the inner and outer cavities, when the attachment is adjacent to the skin tissue, to pull the skin tissue into the cavities and stress the skin tissue adjacent to the inner member.

The three embodiments of the system are particularly suitable for imaging external tissue in different regions of the patient's body. The platen may be used for confocal imaging of skin tissue on the chest or back. The brace may be used for gross anatomical features, such as the arm, leg or torso, around which the straps can hold the brace upon. The attachment is useful for smaller regions of the skin, where there is no gross anatomical feature, or where the surface of the skin tissue in not substantially level.

BRIEF DESCRIPTION OF THE DRAWINGS

The foregoing objects, features and advantages of the invention will become more apparent from a reading of the following description in connection with the accompanying drawings in which.

DETAILED DESCRIPTION OF THE INVENTION

Figure 1:
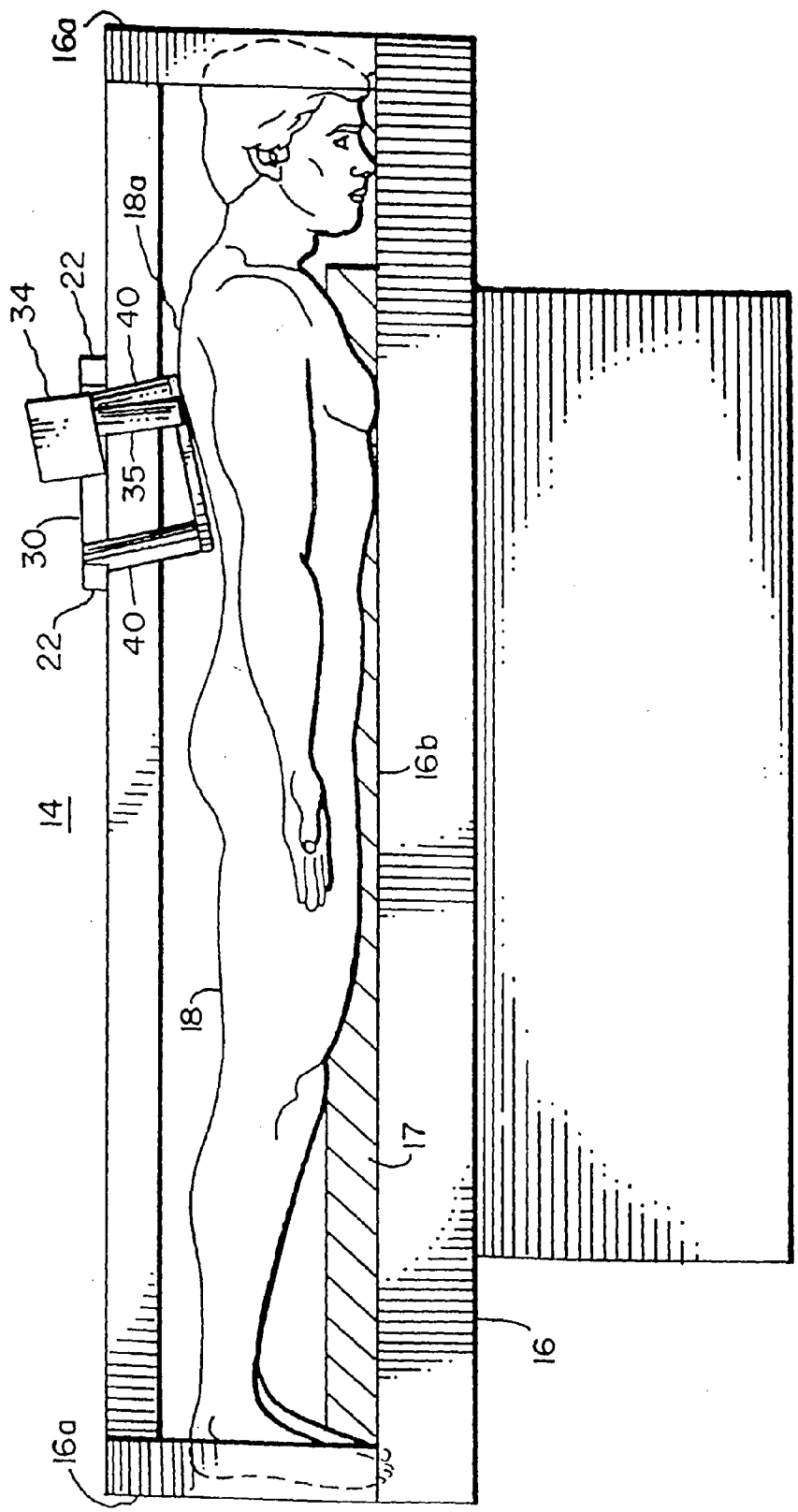
FIG. 1 is a side view of the system in accordance with a first embodiment of the present invention having the platen of the system in a down position.

Referring to FIGS. 1-4, there is shown system 14 including a rigid table 16 with a pad 17 on table surface 16a upon which a patient 18 may lay flat. Pad 17 may be composed of a vinyl-covered cell foam (such as CF 40100 Foam from EAR Specialty Composites of Indianapolis. Ind.) which deforms under the weight of patient 18 and remains deformed for a period of time after the patient has left the table. Table 16 has two parallel rails 20 spaced apart from each other along two opposite sides of table 16, and two parallel rails 22 spaced apart from each other. Rails 20 and 22 are perpendicular to each other, i.e., rails 20 extend in the x direction and rails 22 extend in the y direction.

A platen 30 carrying a confocal imaging head 34 is mounted in a mechanism provided by rails 20 and 22 for movably positioning head 34 to observe dermal tissue of interest in the body of patient 18. This mechanism has a carriage 25 supporting platen 30. Carriage 25 rides along rails 22 across table 16 (as indicated by bidirectional arrow x), and is locked in position with respect to rails 22 by a lock 28, such as a locking screw. Rails 22 and its two spacers 23, which connect rails 22 together, ride along rails 20 up or down table 16 (as indicated by bi-directional arrow y), and are locked in position with respect to rails 20 by a lock 24, such as a locking screw. Thus, platen 30 can then be moved by the operator in two orthogonal directions x and y over patient 18 and temporarily fixed in a desired position.

Figure 4:
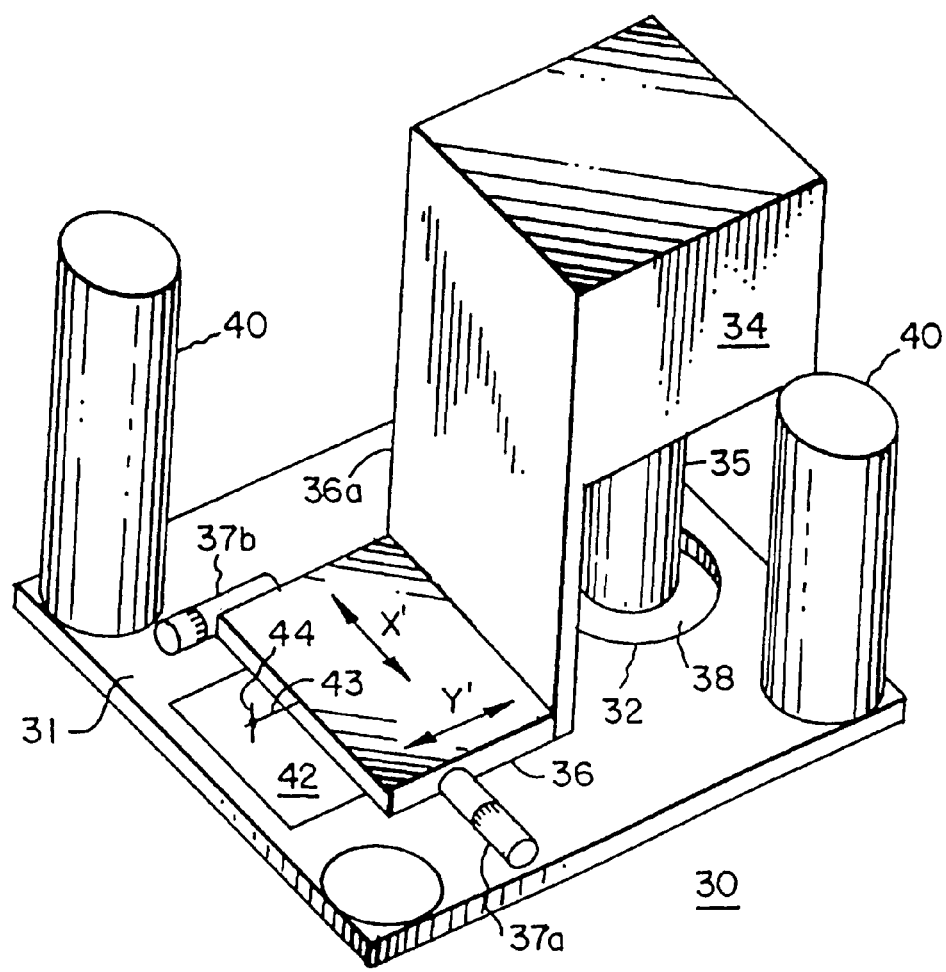
FIG. 4 is a perspective view of the platen of the system of FIG. 1.

Referring to FIG. 4, platen 30 and the head 34 assembly is shown in more detail. Platen 30 is a rigid structure having an upper surface 31 with a translation stage 36 which is mechanically coupled to a confocal imaging head 34 via support 36a. Confocal imaging head 34 has an objective lens 35 positioned over an orifice or opening 32 through platen 30. Confocal imaging head 34 with objective lens 35 are described in U.S. application Ser. No. 08/650,684, filed May 20, 1996, now U.S. Pat. No. 5,788,639, issued Aug. 4, 1998, and assigned to the same assignee as the present invention, and is herein incorporated by reference. Translation stage 36 is movable in two orthogonal directions x' and y' (see arrows x' and y' in FIG. 4) to provide fine resolution positioning (a; compared with coarse positioning of platen 30 via rails 20 and 22) of imaging head 34, and more specifically objective lens 35, with respect to platen 30 over orifice 32. The translation stage 36 has cross rotating ball bearings (not shown) or cross piezoelectric position actuators to facilitate fine resolution movement in orthogonal directions x' and y'. Manual stage micrometers 37a and 37b adjust translation stage 36 in x' and y' directions, respectively. Micrometers 37a and 37b may be substituted by motors which are remotely controlled. A lock (not shown) on translation stage 36 may be provided to temporarily fix the position of stage 30, and consequently imaging head 22, with respect to platen 30. Thus, translation stage 36 defines a means for fine resolution positioning of the objective lens over the orifice. Also, an index matching plate 38 may be positioned within orifice 32 in front of objective lens 35 to form a window which maintains the height stability of the tissue while presenting the edges of orifice 32 to the skin for stressing the tissue.

Figure 2:
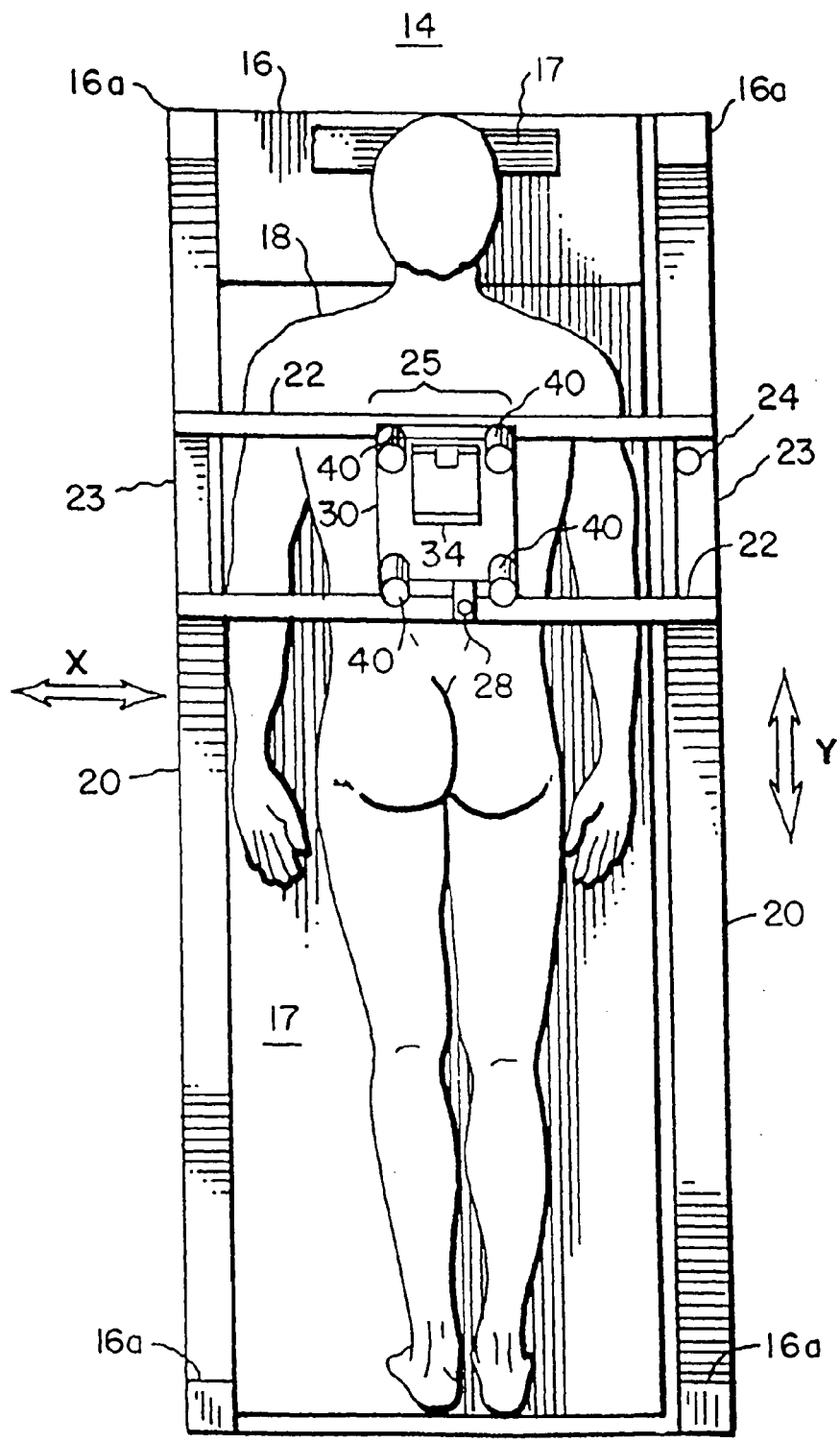
FIG. 2 is a plan view of the system of FIG. 1.
Figure 3:
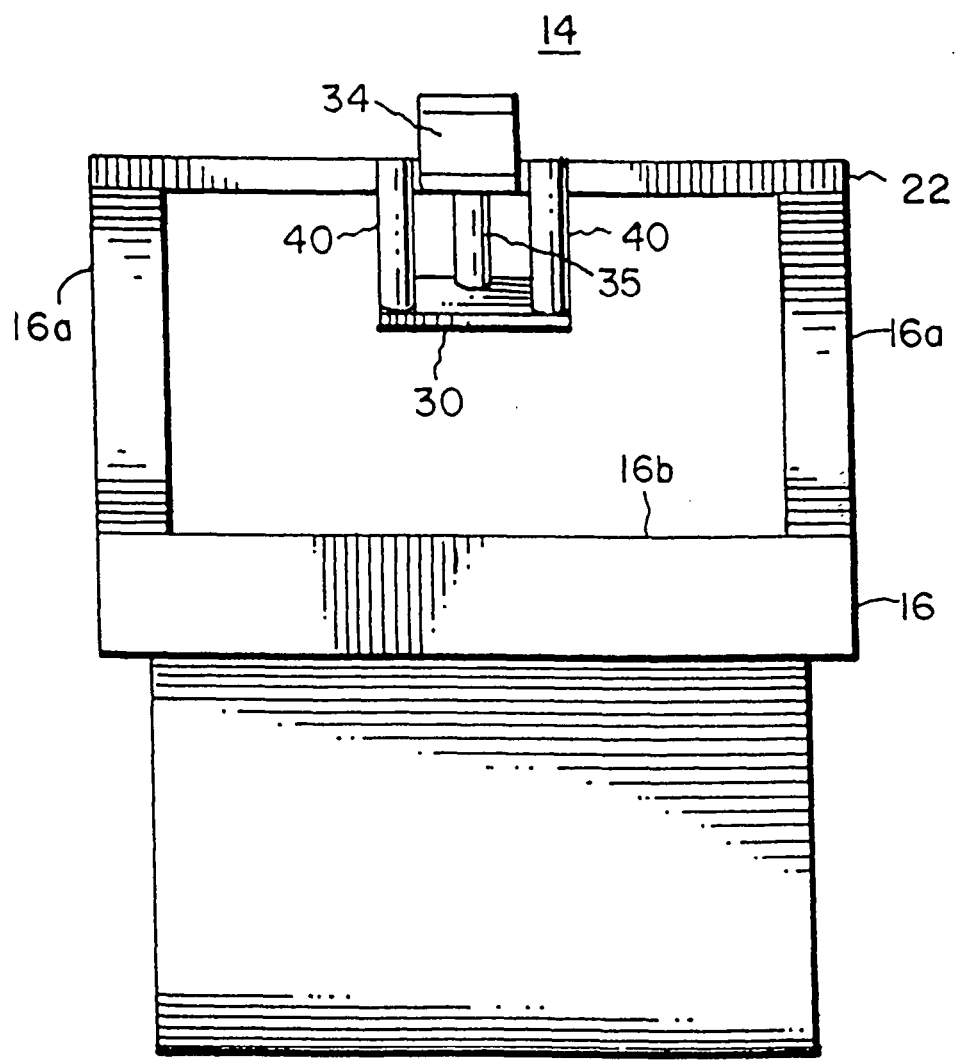
FIG. 3 is a front view of the system of FIG. 1 without the subject patient.

Platen 30 includes four vibration damping rods 40 at the four corners of platen 30 (for purposes of illustration only two rods 40 are shown in FIG. 4). Each damping rod 40 has a lower end coupled to platen 30 and an upper end coupled to carriage 25, as shown in FIGS. 1-3. Thus, damping rods 40 connect platen 30 to carriage 25. Damping rods 40 may be hydraulic type shock absorbers which when released allow platen 30 to gradually move from an up position to a down position upon the patient's skin 14a (such as shown in FIG. 1) and also allow platen 30 to be moved from a down position back to an up position. Locking screws (not shown) on the damping rods 40 may fix the position of platen 30 with respect to carriage 25 in either up or down positions. Damping rods 40 thereby provide a means for moving platen 30 from an up position, in which the platen is spaced from patient 18, to a down position onto surface 18a of skin tissue of the patient.

In operation of system 14, the operator (e.g., a physician) moves rails 22 (i.e., the rails upon which carriage 25 rides) along rails 20 to position platen 30 in the y direction, and moves carriage 25 along rails 22 to position platen 30 in the x-direction such that the volume of skin tissue of interest on patient 18, such as a lesion, will be positioned within orifice 23 of the platen when platen 30 is in a down position. Using locks 24 and 28 described above, the operator locks carriage 25 with respect to rails 20 and 22, thus fixing the position of platen 30 with respect to patient 18. Next, the operator releases damping rods 40 to allow platen 30 to gradually fall by the force of gravity onto the patient's skin. In response to the weight of platen 30, the skin lying within orifice 32 of platen 30 bulges upwards into orifice 32, thereby applying stress to the skin. This stress places the skin in orifice 32 preferably under tension, but may further push the skin up into orifice 32 by compression of skin beneath platen 30. The stress applied to the skin in orifice 32 is substantially due to the downward pressure or force of platen 30 at the edges of orifice 32. Optionally, springs may be located within damping rods 40 to provide additional downward pressure onto the skin. The operator then controls the translation stage movement either directly or remotely to position objective lens 35 of imaging head 34 over area of tissue within orifice 32 desired to be imaged. The operator enables optics within the confocal imaging head to confocally image horizontal, vertical, or angular sections through different planes of the tissue. During confocal imaging, the stress applied to the skin tissue in orifice 32 stabilize the tissue reducing motion of the skin tissue with respect to confocal imaging head 34, thereby stabilizing confocal images scanned by head 34.

Platen 30 may have a paper pad 42 to provide a recording media, and a pen or marker 44 mechanically coupled to translation stage 36 by arm 43 such that pen 44 is suspended over pad 42. Movement of translation stage 36 can thus be recorded by ink from the pen 44 on pad 32. This allows the operator during confocal imaging by imaging head 34 to map the horizontal extent or borders of a lesion in the skin, since pen 44 transfers the motion of translation stage 36 on pad 43 by the fixed geometry which mechanically couples pen 44 to objective lens 23 via arm 43, stage 36, support 36a and imaging head 34. After confocal imaging is complete, imaging head 34 may be replaced by another pen to permit the operator to trace the extent of the lesion recorded on pad 32 onto the surface of the skin.

Further, when platen 30 is in a down position, the operator can place index marks on the skin surface with a pen, or other marking instrument, at notches (not shown) along the sides of orifice 32. These index marks locate both orifice 32 and the relative position of objective lens 35 with respect to the skin surface when confocal imaging is performed. In subsequent examinations, orifice 32 and objective lens 35 can be aligned with these index marks to confocally image the same area of skin, and, for example, observe changes occurring in a skin lesion over time.

Figure 5:
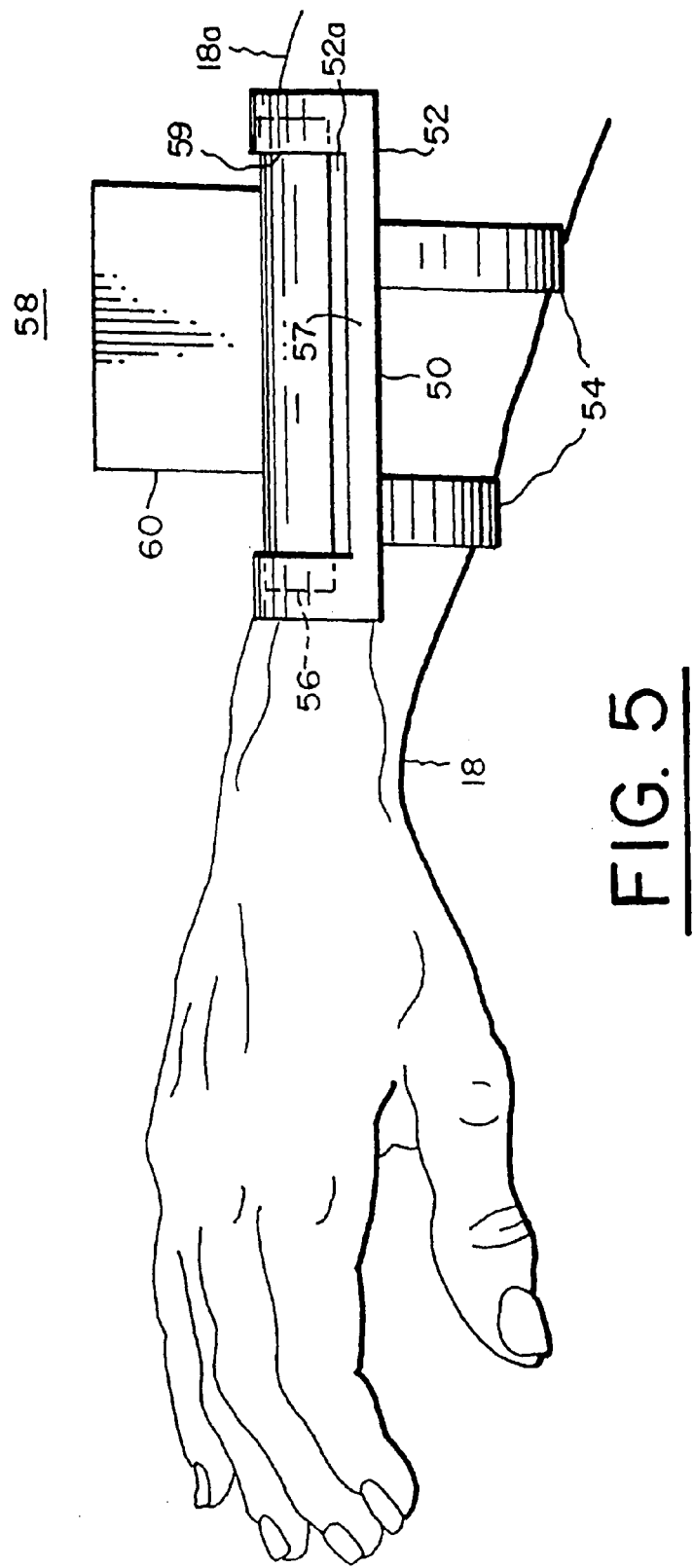
FIG. 5 is a side view of the system in accordance with a second embodiment of the present invention.
Figure 6:
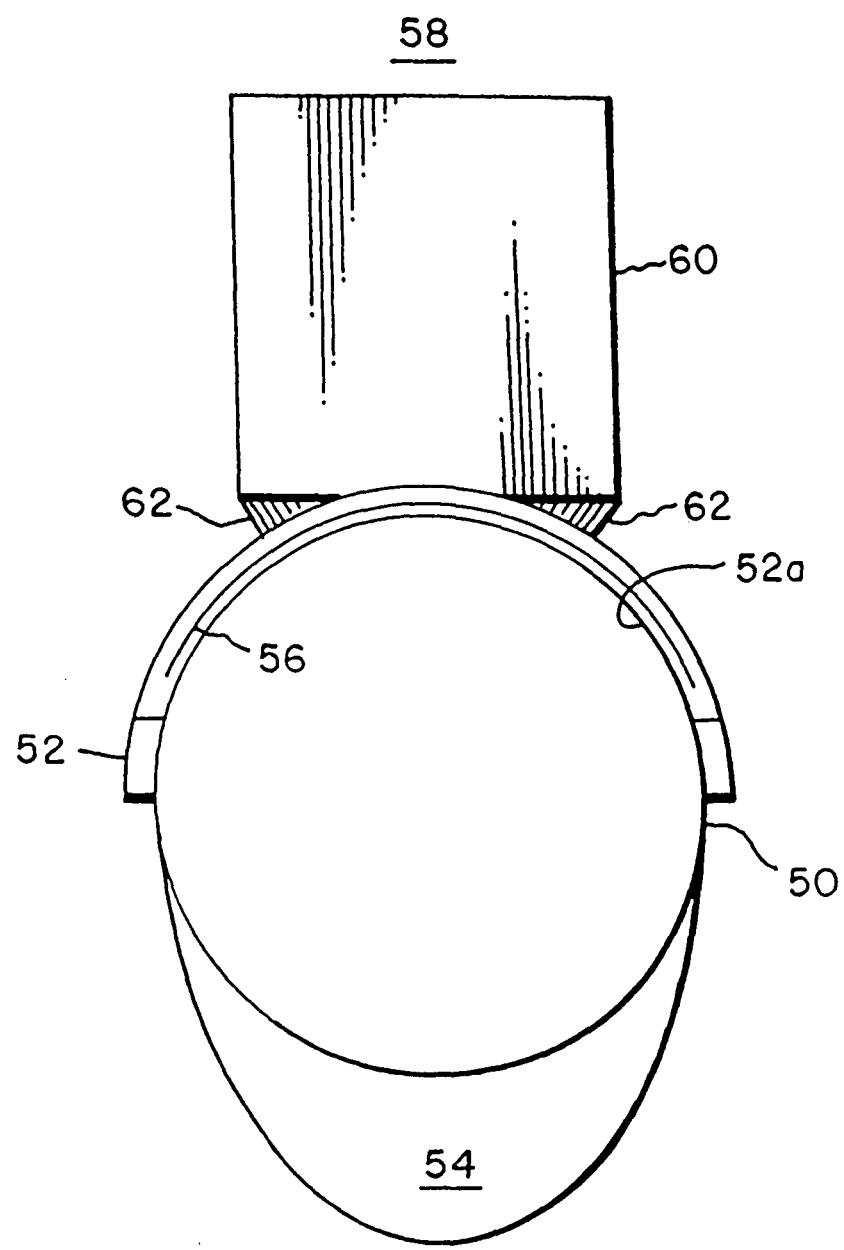
FIG. 6 is a front view of the system of FIG. 5 without the subject skin tissue.
Figure 7:
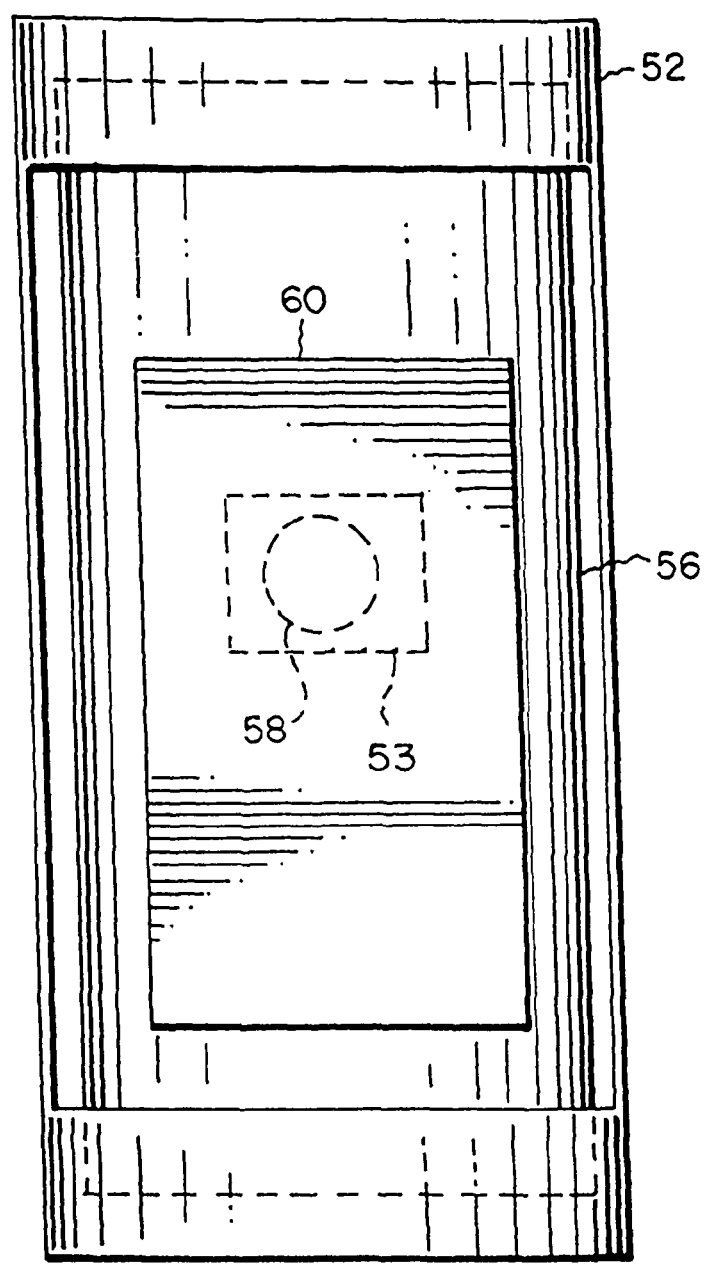
FIG. 7 is a plan view of the system of FIG. 5 without the subject skin tissue.
Figure 8:
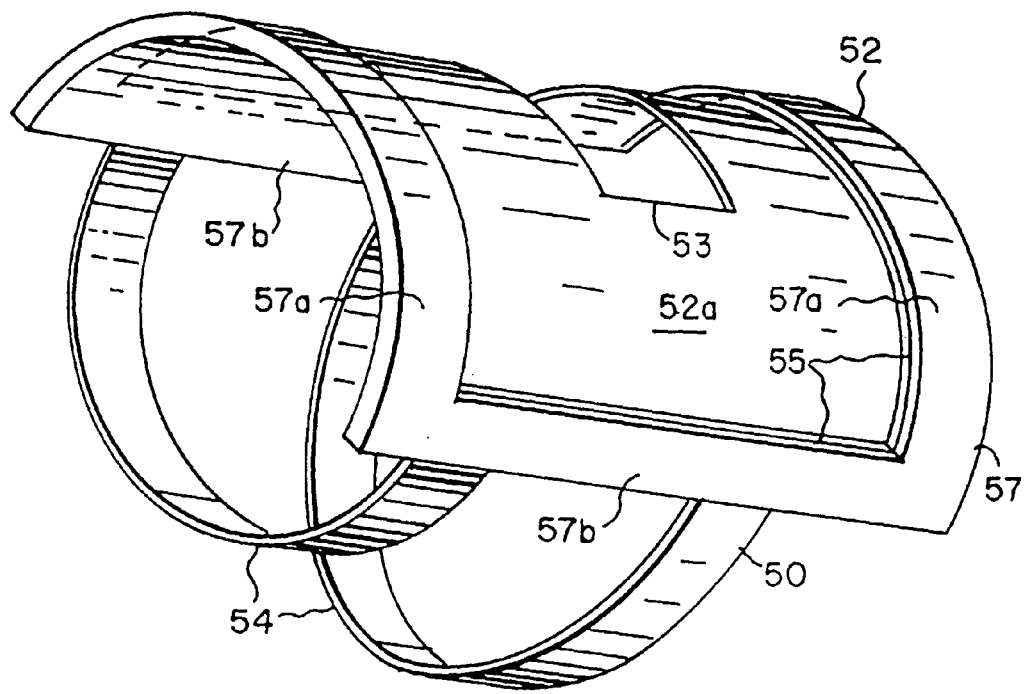
FIG. 8 is a perspective view of the brace structure of the system of FIG. 5 with the upper lamination of the brace structure and confocal imaging head removed.

A second embodiment of the present invention is shown in FIGS. 5-8 having a system 58. System 58 includes a brace structure 50 having a rigid lower lamination 52 which is held stationary to the skin tissue 18a of patient 18 by straps 54. Lower lamination 52 is shaped to approximate the curvature of a gross anatomical body part of the patient, such as part of the leg, torso, or arm, as shown in FIG. 5. A bottom 52a of lower lamination 52 has an opening 53, as shown in FIGS. 7 and 8. Bottom 52a defines a well 59 therein between ends 57a and sides 57b of lower lamination 52. Ends 57a and sides 57b define a rigid frame 57. Further, ends 57a and sides 57b have blind slots 55 within which an upper lamination 56 is captured. FIG. 8 shows frame 57 of lower lamination 52 in which upper lamination 56 has been removed for purposes of illustration.

Upper lamination 56 is a curved rigid sheet parallel with lower lamination 52, and has a confocal viewing window 58 (FIG. 7) substantially smaller than opening 53. Viewing window 58 may be positioned at a location over opening 53 by sliding upper lamination 56 over lower lamination 52 via slots 55 within frame 57. A confocal imaging head 60 is supported on brace structure 50 by gussets 62 (FIG. 6) and has an objective lens (not shown) positioned for imaging through confocal viewing window 58 of upper lamination 56. The window may contain a transparent plate for tissue height stabilization. Confocal imaging head 60 with the objective lens 35 are described in U.S. application Ser. No. 08/650,684, filed May 20, 1996, now U.S. Pat. No. 5,788,639, issued Aug. 4, 1998, and assigned to the same assignee as the present invention, and is herein incorporated by reference. Confocal imaging head 60 is fixably attached to upper lamination 56 and slides therewith over lower lamination 52.

In operation of system 58, brace 50 is first strapped by straps 54 over an anatomical feature, such as an arm, leg, or torso, in which the general skin tissue area to be confocally imaged bulges upward through opening 53 of bottom 52a under the pressure from lower lamination 52, thereby applying stress to the surface of the skin. This stress preferably places the skin through opening 53 under tension, but may further push the skin up into opening 53 by compression of skin beneath lower lamination 52. The stress applied to the skin in opening 53 is substantially due to the pressure or force from lower lamination 52 to the skin tissue at the edges of opening 53. The specific area of the skin to be confocally imaged is then positioned within confocal viewing window 58 by sliding upper lamination 56 over lower lamination 52. Lower lamination 52 provides a sliding surface for upper lamination 56 and slots 55 of frame 57 provide sufficient friction against upper lamination 56 to temporarily fix the position of upper lamination 56 with respect to lower lamination 52 and the skin tissue. Confocal imaging head 60 is then attached to upper lamination 56 of brace 50 to position the confocal optics of head 60, i.e., its objective lens, through confocal imagine window 58. When enabled, these confocal optics within imaging head 60 can confocally image horizontal, vertical, or angular sections through different planes of the tissue through confocal viewing window 58. Thus, brace 50 locates confocal imaging head 60 in fixed relationship with the skin tissue, and window 58 defines an aperture through brace 50 for imaging via optics of head 60.

By attaching imaging head 60 to upper lamination 56, head 60 moves with motion of the skin tissue since such motion is transferred to head 60 via brace structure 50. This reduces the relative motion of the tissue held under stress with respect to the confocal optics of imaging head 60 to minimize instability of the confocal images from imaging head 60. Upper lamination 56 may be moved to reposition the confocal imaging optics of head 60 through window 58 for confocal imaging of other areas of skin tissue within opening 53.

Figure 9:
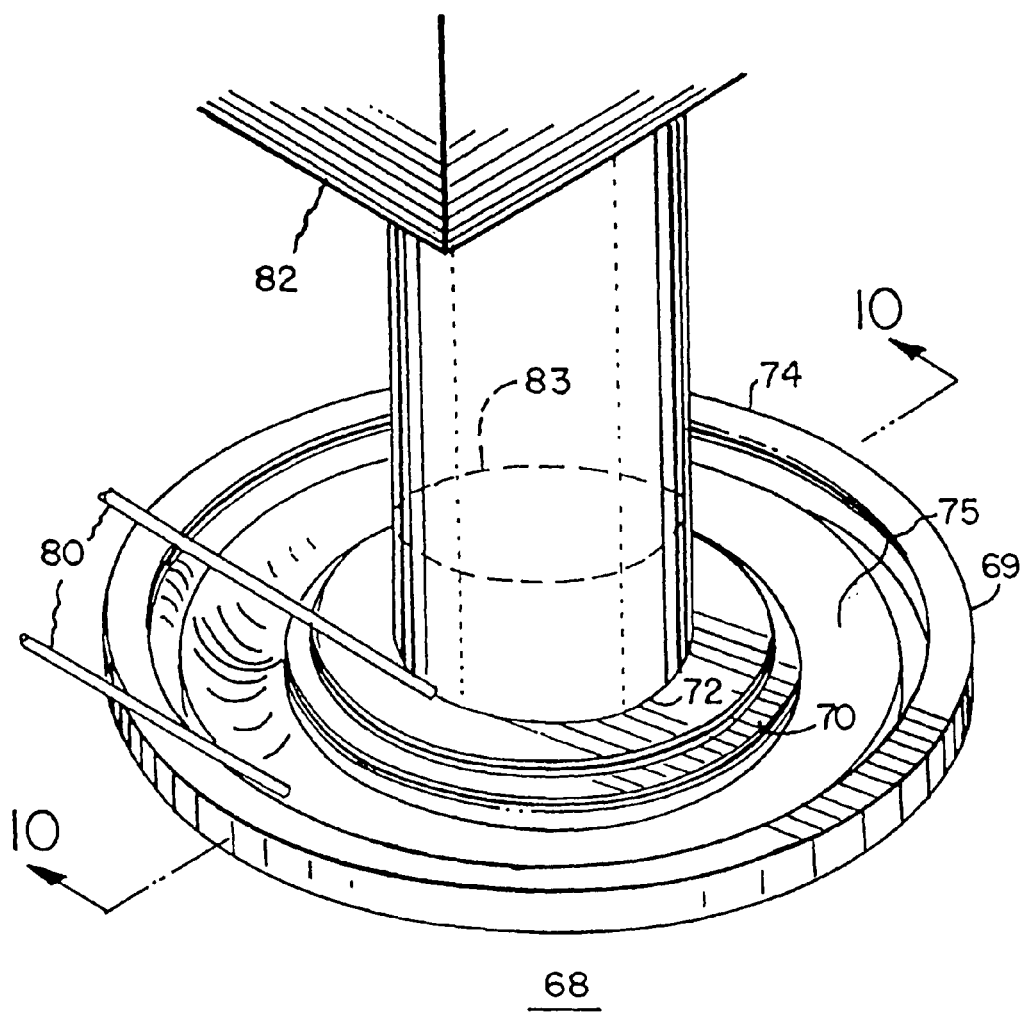
FIG. 9 is a perspective view of the system in accordance with a third embodiment of the present invention.
Figure 10:
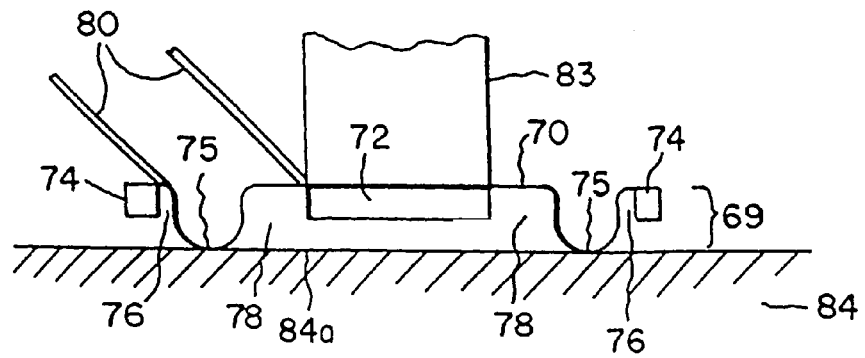
FIG. 10 is a cross-sectional view of the system along line 10-10 of FIG. 9 when the attachment of the system is not engaging skin tissue.
Figure 11:
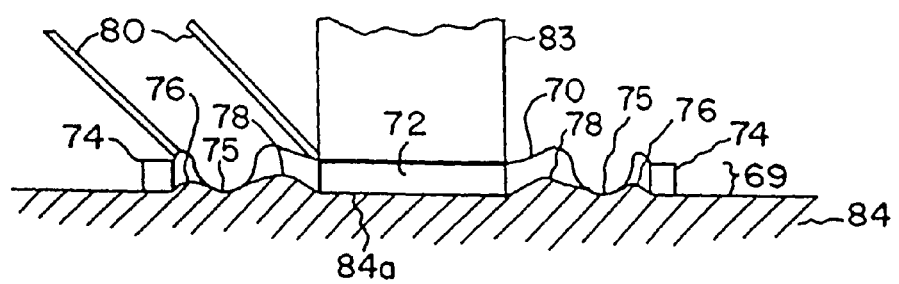
FIG. 11 is another cross-sectional view of the system along line 10-10 of FIG. 9 when the attachment of the system is engaging skin tissue.

A third embodiment of the present invention is shown in FIGS. 9-11. This embodiment is provided by a tissue stabilization system 68 which includes an attachment 69. The tissue is shown at 84 in FIGS. 10-11 as a layer of skin. Attachment 69 includes a flexible diaphragm member 70, a central circular window or plate member 72, and a semi-rigid ring 74. Diaphragm 70 is composed of deformable rubber selected to be less compliant than tissue 84. Diaphragm 70 radially extends from window 72 outward to semi-rigid ring 74. Ring 74 may be composed of hard rubber, while window 72 may be composed of a material having an optical index approximately matching tissue 84. Diaphragm 70 has between ring 74 and window 72 an annular protruding section 75 (protruding in the direction of the arrow of FIG. 10). Section 75 defines outer and inner annular cavities 76 and 78, respectively. Also, attachment 69 has a pair of vacuum lines 80 which each connects different ones of annular cavities 76 and 78 to a pneumatic pump which selectively creates suction between diaphragm 70 and the surface 84a of tissue 84. The size or diameter of system 68 and its attachment 69 may be appropriately dimensioned for the skin surface area to be confocally imaged through window 72.

System 68 further includes a confocal imaging head 82 having an objective lens 83 positioned such that lens 83 is directed to window 72 of attachment 69. Confocal imaging head 82 with objective lens 83 are described in U.S. application Ser. No. 08/650,684, filed May 20, 1996, now U.S. Pat. No. 5,788,639, issued Aug. 4, 1998, and assigned to the same assignee as the present invention, and is herein incorporated by reference. Objective lens 83 is shown in phantom lines in FIG. 9, and the dotted lines in the figure represent the optical imaging paths between lens 83 and other confocal optics within imaging head 82. For example, these optical imaging paths may be provided within an extending snout between head 82 and objective lens 83.

In operation, attachment 69 is first placed over surface 84a of tissue 84 such that diaphragm protruding section 75 is adjacent to surface 84a, as shown in FIG. 10. When window 72 is located over the area of tissue 84 to be confocally imaged, the air is evacuated via vacuum lines 80 from each cavity 76 and 78. This creates suction which pulls tissue 84 up into cavities 76 and 78, as shown in FIG. 11. As a result, semi-rigid ring 74 and window 72 are pulled downward onto surface 84, and the tissue beneath window 72 is placed under stress, such as by tension or compression. In this mode, attachment 69 engages or adheres by suction to the surface 84a of the tissue.

Next, objective lens 83 of confocal imaging head 82 is placed against window 72 for confocal imaging of tissue 84 below window 72, then the confocal optics within imaging head 60 are enabled to provide confocal images of horizontal, vertical and angular sections through different planes of the tissue. Optionally, attachment 69 may be fixedly attached to head 82 in front of its objective lens 83 prior to placing attachment 69 adjacent to the skin tissue. Since the tissue being confocally imaged is held under stress by attachment 69 under window 72, the relative motion of this tissue with respect to the confocal optics within imaging head 82 is reduced, thereby stabilizing confocal images from head 82. When imaging is complete, air is allowed to flow back into cavities 76 and 78 via vacuum lines 80, allowing attachment 69 to disengage from the surface 84a of the tissue.

Alternatively, a liquid on the surface 84a of the tissue may be evacuated via vacuum lines 80 (in combination with or instead of air) from cavities 76 and 78. Such a liquid may be applied to the surface 84a of the tissue prior to placing attachment 69 over the surface.

Each of the three embodiments of the present invention is particularly suitable for imaging external tissue in different regions of the patient's body. The first embodiment may be used for confocal imaging of skin tissue on the chest or back, while the second embodiment may be used, for gross anatomical features, such as the arm or leg, around which straps can hold brace structure 50 upon. Further, the third embodiment is useful for smaller regions of the skin, particularly where there is no gross anatomical feature, or where the surface of the skin tissue in not substantially level, such as the cervix or forehead. Each of the above confocal imaging system embodiments provides a mechanism for maintaining an area of skin tissue being confocal imaged under a stressed configuration by tension or compression, thereby minimizing the motion of this area with respect to a confocal imaging head. In the cervix the tissue being imaged is not skin as that term is commonly understood, but represents internal tissue of a patient. Internal tissues, for example which are surgically exposed, may be stabilized using the invention.

From the foregoing description, it will be apparent that there have been provided several embodiments of a confocal imaging system for dermatological pathology applications. Variations and modifications of the herein described system and other applications for the invention will undoubtedly suggest themselves to those skilled in the art. Accordingly, the foregoing description should be taken as illustrative and not in a limiting sense.

What is claimed is:

1. A system for recording on a recording medium the location of one or more tissue sections imaged by a microscope, said system comprising:
   a microscope for imaging in-vivo tissue of a body of a patient to provide one or more images of one or more tissue sections;
   means for moving a part of said microscope and the body of the patient with respect to each other in one or more directions during imaging to view different parts of the in-vivo tissue of the patient with said microscope; and
   means for applying force to the body of the patient to stabilize the tissue when imaged by said microscope, and said means for applying force having an opening that restricts the extent of the stabilized tissue presentable to the microscope for imaging to that within said opening;
   means, coupled to said moving means, for recording on a recording medium information associated with one or more locations of the in-vivo tissue of the patient of said one or more images of tissue sections.

2. The system according to claim 1 further comprising means for applying said recorded information onto the surface of said tissue to indicate the one or more recorded locations of the one or more tissue sections upon the surface of said tissue through which the one or more tissue sections were imaged.

3. The system according to claim 1 wherein said one or more locations represents recordable information as to an extent of a lesion in said imaged tissue.

4. The system according to claim 1 said recording means is movable with respect to said recording medium to enabling recording of said information.

5. The system according to claim 1 wherein said microscope comprises optics through which said microscope images said tissue, and said means for moving comprises a stage coupled to said optics for moving said optics in one or more directions during imaging to view said tissue with said microscope.

6. The system according to claim 5 wherein said stage has one or more micrometers to manually control the stage to position said optics in said one or more directions.

7. The system according to claim 5 wherein said stage is remotely controlled by motors to position said optics in said one or more directions.

8. The system according to claim 5 wherein said means for recording comprises a pen or marker mechanically coupled to said stage to be movable in accordance with movement of said stage, said pen or marker being disposed with respect to said recording medium to apply ink to said recording medium to record one or more locations of said optics with respect to said imaged tissue.

9. A method for recording on a recording medium the location of one or more tissue sections imaged by a microscope, said method comprising the steps of:
   moving with respect to each other a part of a microscope that images one or more tissue sections of in-vivo tissue, and a body of a patient, in one or more directions during imaging to view different parts of the in-vivo tissue of the patient;
   stabilizing said tissue when imaged by the microscope using a device that applies force to the body of the patient and has an opening which restricts the extent of the stabilized tissue presentable to the microscope for imaging to that within said opening; and
   recording on a recording medium positional information relative to said in-vivo tissue of one or more tissue sections imaged by the microscope.

10. The method according to claim 9 further comprising the step of applying said positional information onto the surface of said tissue to indicate the one or more recorded locations of the one or more tissue sections upon the surface of said tissue through which the one or more tissue sections were imaged.

11. The method according to claim 9 wherein said recording step further comprising recording on the recording medium one or more locations to provide information mapping a structure in the tissue existing in the body of the patient when said one or more location were recorded.

12. An apparatus for recording on a recording medium the location of one or more tissue sections imaged by a microscope, said apparatus comprising:
- a microscope which images in-vivo tissue of a body of a patient;
- a device which applies force to the body of the patient to stabilize the tissue when imaged by said microscope, wherein said device has an opening and restricts the extent of the stabilized tissue presentable to the microscope for imaging to that within said opening;
- a recording medium disposed on a surface positionally related to the surface of the tissue through which said microscope images the in-vivo tissue of the body of the patient; and
- a pen or marker to mark on said recording medium positional information relative to the tissue imaged by the microscope.

13. The apparatus according to claim 12 wherein said microscope comprise an objective lens.

14. The apparatus according to claim 12 wherein said positional information is recordable onto the surface of said tissue imaged by said microscope.

15. The apparatus according to claim 12 wherein said positional information is associated with a structure in the tissue existing in the body of the patient when said positional information was recorded on said recording medium.

16. The apparatus according to claim 12 wherein:
- said device comprises a bottom surface for placing the tissue under stress by application of force by said bottom surface against the body of the patient to stabilize the tissue when imaged by said microscope; and
- said opening is located in said bottom surface.

17. The apparatus according to claim 16 wherein said device has a material window in said opening, and said application of force against the body of the patient is provided by at least said bottom surface and said window against the tissue.

18. The apparatus according to claim 12 wherein said device comprises a first device, and said apparatus further comprises a second device for recording on said tissue said positional information which was recorded by said pen or marker on said recording medium.

19. An apparatus for recording on a recording medium the location of one or more tissue sections imaged by a microscope, said apparatus comprising:
- a microscope which comprises optics through which said microscope images in-vivo tissue of a body of a patient to provide one or more images of one or more tissue sections;
- a first device which with applied force to the body of a patient stabilizes the in-vivo tissue with respect to said optics, wherein said first device has an opening that restricts the extent of the stabilized tissue presentable to the microscope for imaging to that within said opening;
- a recording medium; and
- a second device linked to said microscope to record on said recording medium one or more positions relative to said optics with respect to said stabilized tissue by said first device during capture of the images of the one or more tissue sections by said microscope.

20. The apparatus according to claim 19 wherein said one or more positions recorded on said recording medium enable a user to record said one or more positions upon the tissue imaged by the microscope.

21. The apparatus according to claim 19 wherein said recording medium is locatable on said first device.

22. The apparatus according to claim 19 wherein said one or more recorded positions on said recording medium are associated with structure of the tissue in said images, and said one or more recorded positions are recordable onto said tissue to enable a user to locate the structure in the tissue associated with said one or more recorded positions.

23. The apparatus according to claim 19 wherein at least one of said one or more images is an image of a tissue section below the surface of the tissue.

24. The apparatus according to claim 19 wherein said second device provides a marking device associated with said recording medium.

25. The apparatus according to claim 19 wherein said recording medium is located outside the view of said tissue by said optics.

26. The apparatus according to claim 19 wherein said optics comprises an objective lens directed towards the tissue, and said first device and said objective lens are movable with respect to each other.

27. The apparatus according to claim 26 wherein movement of said first device and said objective lens with respect to each other in one or more dimensions is transferred into movement of said second device for recording and said recording medium with respect to each other.

28. The apparatus according to claim 19 wherein:
- said first device comprises a bottom surface for placing the tissue under stress by application of force by said bottom surface against the body of the patient to stabilize the tissue with respect to said optics; and
- said opening is located in said bottom surface.

29. The apparatus according to claim 28 wherein said first device has a window of a material in said opening, and at least said bottom surface and said window provides said application of force against the body of the patient.

30. The apparatus according to claim 19 further comprising a third device for recording upon said tissue said one or more positions recorded by said second device relative to said captured images of said one or more tissue sections by said microscope.

31. A system for recording on a recording medium the location of one or more tissue sections imaged by a microscope, said system comprising:
- a microscope which comprises optics through which said microscope images tissue to produce images of one or more tissue sections;
- a recording medium;
- a first device linked to said microscope to record on said recording medium one or more positions relative to said optics with respect to the tissue during capture of one or more images of one or more tissue sections by said microscope;
- a second device for recording one or more locations upon said tissue imaged by said microscope in which said one or more locations are recorded upon said tissue in accordance with the one or more positions recorded by said first device on said recording medium to enable a user to locate structure present in said one or more images of said one or more tissue sections; and
- a third device attachable to said microscope having a bottom surface for placing the tissue under stress by application of force by said bottom surface against the body of the patient to stabilize the tissue with respect to said optics, wherein said third device has an opening in said bottom surface, and said opening restricts the extent of the stabilized tissue presentable to said microscope for imaging to that within the opening.

32. The apparatus according to claim 31 wherein said third device is separable from said optics, and wherein said third device has a material window in said opening and said application of force against the body of the patient is provided by at least said lower surface and said window against the tissue.

* * * * *